(12) United States Patent
Bedell, Jr.

(10) Patent No.: US 12,708,301 B2
(45) Date of Patent: Aug. 18, 2026

(54) DIGITAL HEALTH SYSTEM FOR THE CONTINUOUS QUANTIFICATION OF PHYSIOLOGICAL BIOMARKERS, BIOLOGICAL REGULATORS, AND ANALYTES IN REAL-TIME USING OPTICAL QUANTIFICATION

(71) Applicant: Alfred H. Bedell, Jr., Lansdowne, PA (US)

(72) Inventor: Alfred H. Bedell, Jr., Lansdowne, PA (US)

( * ) Notice: Subject to any disclaimer, the term of this patent is extended or adjusted under 35 U.S.C. 154(b) by 1245 days.

(21) Appl. No.: 16/928,714

(22) Filed: Jul. 14, 2020

(65) Prior Publication Data

US 2020/0337621 A1 Oct. 29, 2020

Related U.S. Application Data

(62) Division of application No. 15/887,748, filed on Feb. 2, 2018, now Pat. No. 10,772,552.

(Continued)

(51) Int. Cl.
*A61B 5/16* (2006.01)
*A61B 5/00* (2006.01)

(Continued)

(52) U.S. Cl.
CPC ............ *A61B 5/165* (2013.01); *A61B 5/0004* (2013.01); *A61B 5/02416* (2013.01); *A61B 5/0533* (2013.01); *A61B 5/14546* (2013.01); *A61B 5/14552* (2013.01); *A61B 5/681* (2013.01); *G16H 10/40* (2018.01); *G16H 50/20* (2018.01); *G16H 50/30* (2018.01); *A61B 5/02055* (2013.01); *A61B 5/18* (2013.01);

(Continued)

(58) Field of Classification Search
CPC ... A61B 5/165; A61B 5/0004; A61B 5/02416; A61B 5/0533; A61B 5/14546; A61B 5/14552; A61B 5/681; A61B 5/02055; A61B 5/18; A61B 2560/0223; G16H 10/40; G16H 50/20; G16H 50/30; G01N 33/48792

See application file for complete search history.

(56) References Cited

U.S. PATENT DOCUMENTS

2009/0177068 A1* 7/2009 Stivoric ............... A61B 5/0022 600/365
2013/0172698 A1* 7/2013 Reynolds ......... A61B 5/150755 600/316
2016/0174853 A1 6/2016 Cho et al.

* cited by examiner

*Primary Examiner* — Abid A Mustansir
(74) *Attorney, Agent, or Firm* — COOLEY LLP

(57) ABSTRACT

A wearable device for the quantification of regulatory substances produced in the body, such as analytes and hormones, is disclosed. The wearable device includes contact sensors formed on an outer portion of a casing of the wearable device, and those contact sensors are positioned to contact skin of a wearer of the device and configured to measure galvanic skin response and temperature. The wearable device also includes a microprocessor in the casing of the wearable device adapted to control programs and execute algorithms, a system memory in the casing of the wearable device adapted to store data, an entry port in the casing of the wearable device adapted to receive a biological-assay cartridge containing a biological sample, and a biological-assay reader placed inside the casing of the device, which includes multiple light sources and detectors for identifying the concentration of an analyte by measuring light reflected from the light source.

12 Claims, 15 Drawing Sheets

Related U.S. Application Data

(60) Provisional application No. 62/454,284, filed on Feb. 3, 2017.

(51) Int. Cl.

| | |
|---|---|
| ***A61B 5/0205*** | (2006.01) |
| ***A61B 5/024*** | (2006.01) |
| ***A61B 5/0533*** | (2021.01) |
| ***A61B 5/145*** | (2006.01) |
| ***A61B 5/1455*** | (2006.01) |
| ***A61B 5/18*** | (2006.01) |
| ***G01N 33/487*** | (2006.01) |
| ***G16H 10/40*** | (2018.01) |
| ***G16H 50/20*** | (2018.01) |
| ***G16H 50/30*** | (2018.01) |

(52) U.S. Cl.

CPC *A61B 2560/0223* (2013.01); *G01N 33/48792* (2013.01)

DIGITAL HEALTH SYSTEM FOR THE CONTINUOUS QUANTIFICATION OF PHYSIOLOGICAL BIOMARKERS, BIOLOGICAL REGULATORS, AND ANALYTES IN REAL-TIME USING OPTICAL QUANTIFICATION

CROSS-REFERENCE TO RELATED APPLICATIONS

This application is a divisional application and claims the benefit of U.S. application Ser. No. 15/887,748 filed on Feb. 2, 2018, the disclosure of which is hereby incorporated by reference in its entirety. Application Ser. No. 15/887,748 claims the benefit of U.S. Provisional Application No. 62/454,284, filed on Feb. 3, 2017, the entirety of which is hereby incorporated by reference.

FIELD OF THE INVENTION

The present invention relates generally to the technical field of mobile health devices, and more particularly to the technical field of quantification of biological analytes and hormones. The present invention also relates to the integration of remote health data into a mobile platform.

SUMMARY OF THE INVENTION

The proposed technology is a mobile health system designed to specifically offer consumers a private, discrete, non-invasive, wearable device and smartphone application for the quantification of regulatory substances produced in the body, such as analytes and hormones. The proposed system will detect triggers that stimulate physiological and biological changes in users over the course of time. If successful, the biometric data, recorded by the wearable device and transmitted to a mobile integrated computer device, will give physicians and counselors vital information to develop effective treatment plans and recovery support strategies for patients. The current disclosed technology is an integrated system to monitor the biological regulators (analytes) of individuals using API (application program interface) calls via a mobile integrated computer device. The device may have multiple sensors to monitor the biometrics of the wearer and may assist in detecting triggers that stimulate various physiological and biological changes in an individual, such as stress. The device may also contain an entry port adapted to receive a biological-assay cartridge containing a biological sample, and a biological-assay reader configured to read the biological sample using multiple light sources and detectors to identify a concentration of an analyte in the biological sample by measuring light reflected from the light source.

Case Study

It was demonstrated in various studies such as the "Stress and alcohol: Epidemiologic evidence" article of Keyes et al. (2012) that people who are often stressed are more likely to be diagnosed with Alcohol Use Disorders (AUD) than people who are less stressed. Also, the results of the research conducted by Pohorecky (1991) titled "Stress and alcohol interaction: An update of human research" stated that a high level of stress may lead to an excessive intake of alcohol. Previous research has suggested that when alcohol is available and stress levels are high, individuals will consume alcohol as a means to remediate stress. Veterans who have been identified as having post-traumatic stress disorder (PTSD) were studied to have a higher risk of developing AUD when compared to the general population. Alcohol dependency studies regarding animals have been able to suggest and support possible relationships between stress and alcohol consumption. Such studies believe that animals consumed alcohol because they understood that stress was inescapable.

The classification of stress is typically thought of as the biological reaction to external stimuli that alters the homeostasis of an individual. Stressors may take the form of physiological, social, or psychological events. When stressors are introduced to an individual, several biological events will occur to counteract the tension. First, the hypothalamus gland will secrete a hormone called "Corticotropin Releasing Factor" (CRF). As CRF migrates into the blood, it initiates several physiological episodes. It causes the pituitary gland to facilitate the deliverance of adrenocorticotropin hormone (ACTH), and then ACTH will signal the release of the glucocorticoid hormones from the adrenal glands. The activity of the hypothalamic-pituitary-adrenal (HPA) axis is intended to provide the body with a mechanism to respond to stressors. As the hormone cortisol is released, it increases glucose (sugar) in the blood and the rapid chemical processing of fats and proteins (amino acids). This, in turn, provides excess energy for muscles to respond to the stimulus (stressor). This phenomenon known as the "stress response" can be characterized by changes in body temperature, heart rate, and physiological-arousal state. It is possible to quantify these physiological biomarkers and measure their relationship to the onset of stress triggers. It is also possible to extract the hormone cortisol from biological samples (e.g., saliva, blood, sweat) of participants.

It is highly probable that stress is a factor in the development of AUD. Previous studies were unsuccessful in characterizing the relationship between stress and alcohol due to the apparent limitations of psychometric evaluation of stress and alcohol usage. Participants may selectively self-report their limited interactions with alcohol, and the documented inconsistencies may not match the associated stressors. Also, biases of the research as to the determination of which stressors to measure may alter the relationship between stress and alcohol consumption.

The proposed technology is a health-monitoring device that will track biological regulators and analytes (e.g., cortisol hormone) levels in real-time. The system, with the proposed trademarked name U-Check-It™, will provide a platform for instantaneous biofeedback about the ways participants will respond to multiple stressors and to record the behaviors caused by these stressors. Using U-Check-It™ will allow a third party to continuously monitor the physiological stress biomarkers of individuals at point of care (POC) in an uncontrolled environment. U-Check-It™ will provide portable biological sensors to monitor the biometrics of the wearer, and to assist in detecting triggers that stimulate alcohol consumption and increases in stress levels. The proposed system can ultimately help reduce the rates of AUD, thus reducing health costs in the United States and worldwide.

DETAILED DESCRIPTION OF THE INVENTION

Figure 1:
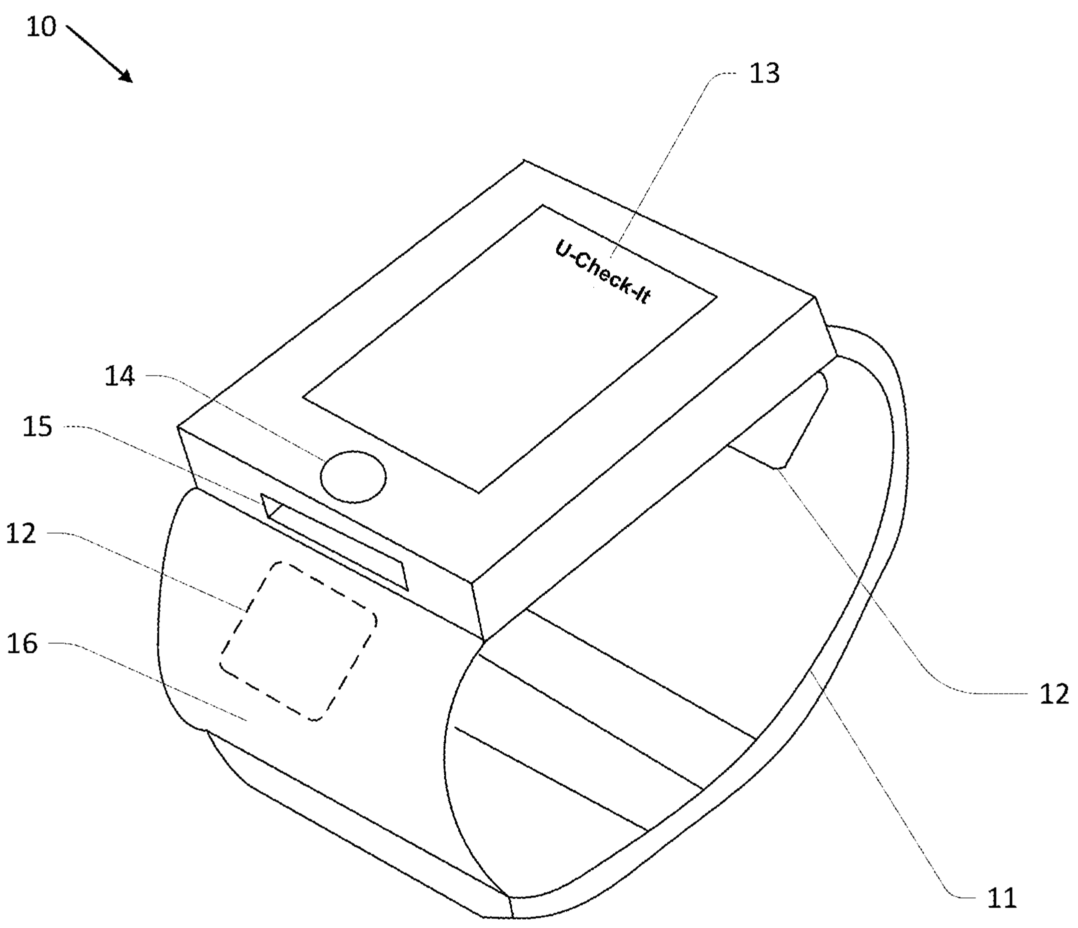
FIG. 1 is a perspective view of the proposed wearable device for the digital health system.

FIG. 1 shows the wearable device (10). The wearable device is a non-invasive digital health device, e.g., a smart wristwatch, capable of measuring biometrics. The wearable device can be attached to the body of the wearer by using the strap (11).

The wearable device will have contact sensors (12) formed on an outer portion of a casing of the wearable device, as shown in FIG. 1 on the strap (11). The contact sensors will be positioned to contact the skin of a wearer of the device and will be configured to measure galvanic skin response and temperature. The contact sensors (12) may be located on the strap (11), or on a flange (16) on the casing of the wearable device, or on the casing itself.

The wearable device will have a display (13), which will be integrated into the wearable device and will be used to communicate relevant information to users about the sensors' performance.

The display will preferably be an OLED (organic light-emitting diode) display: compared to LCD displays, OLED has several advantages such as better power efficiency, lighter weight and flexibility, and faster response time.

The wearable device will have a sensor-node interface (14), which is a customizable docking port for additional sensors for various services (e.g., alcohol sensor, pulse sensor, infrared (IR) camera). As new sensors are developed, they will be able to integrate with the proposed technology via the sensor-node interface. The sensor-node interface may be a USB connection, a mini-USB connection, or any other suitable electrical or electronic interface.

The wearable device will also have a system memory in the casing of the wearable device, and the system memory will be adapted to store data.

Figure 2:
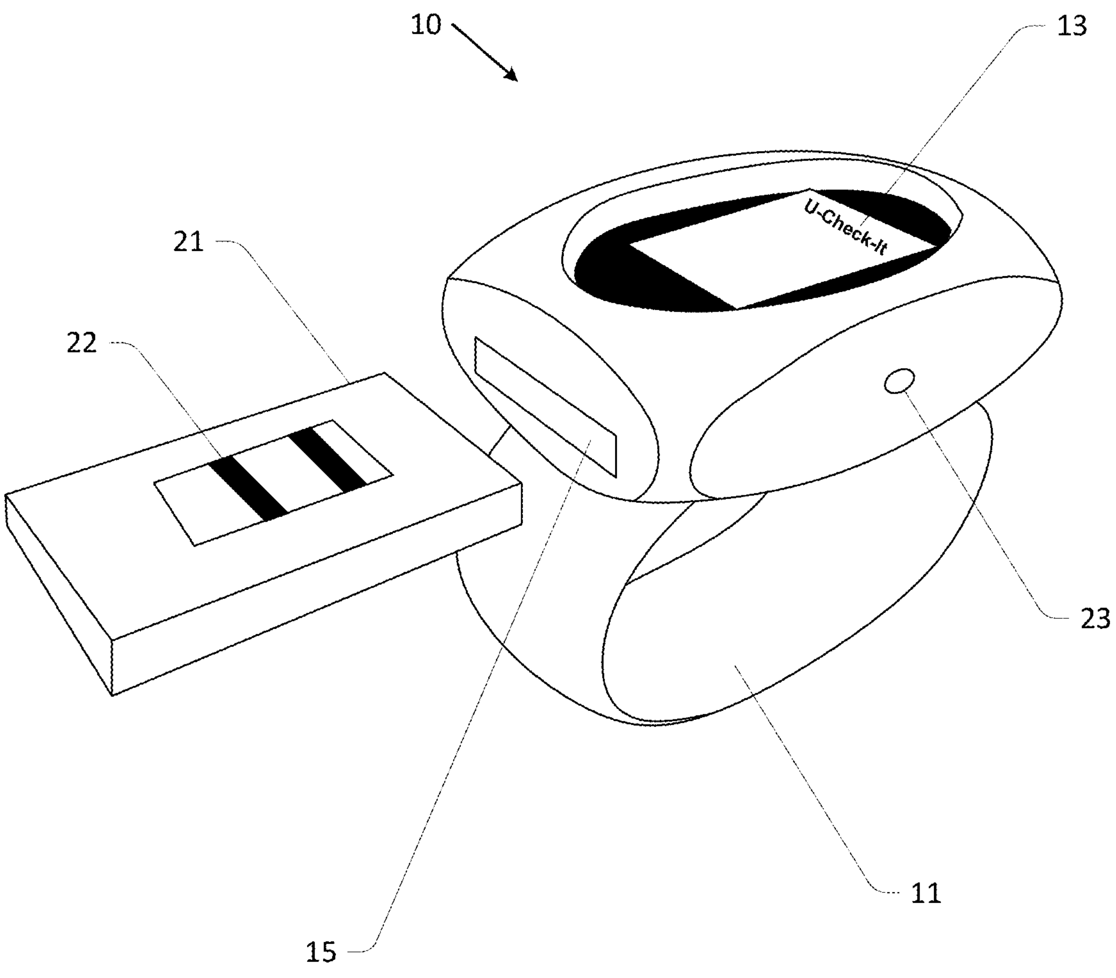
FIG. 2 is a perspective view of the biological-assay cartridge entering the wearable device.

FIG. 2 shows the biological-assay cartridge (21) entering the wearable device via the biological-assay-reader entry port (15). The quantification of hormones or biological analytes will be conducted with a biological-assay cartridge. The biological-assay cartridge will be loaded into the biological-assay-reader entry port for evaluation by the wearable device.

The biological-assay cartridge will be used to measure the amount of specific analytes within a user's biological sample. The biological-assay cartridge may be similar to immunochromatographic assay diagnostic tests such as home-ovulation tests. The user will apply a biological sample (e.g., blood, saliva, urine) to the biological-assay cartridge and insert it into the biological-assay-reader entry port (15). Once inside the wearable device (10), the biological-assay cartridge will undergo systematic processes on a test line (22) for the quantification of the specific analyte or hormone of interest. The biological-assay cartridge and the test line (22) will be consumable products.

This method for analyte quantification is easy to use and the samples are reliable. Current over-the-counter diagnostic tests such as ovulation tests allow simple analysis of a specific analyte in the privacy of one's home. The method of testing does not require a skilled technician or extended educational qualification. In addition, the process does not require expensive machinery or reagents. The current disclosed device will allow end users to quantify their physiological and biological samples in real-time at the point of care (POC). This will provide a non-invasive digital health platform to assist in detecting triggers that stimulate various physiological changes over time.

The charging port (23) will allow a user to recharge the power storage device, such as a battery, and update features to the wearable device.

Figure 3:
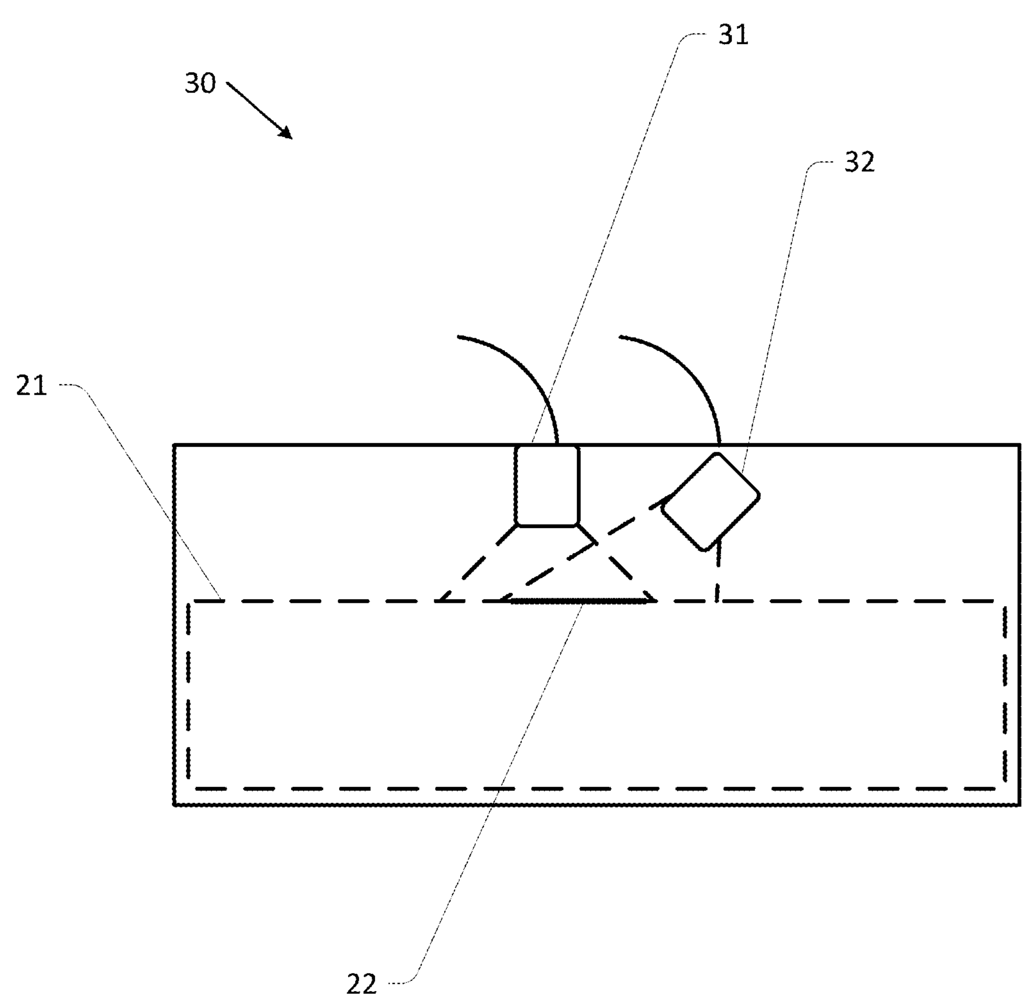
FIG. 3 is a cross-sectional side view of the biological-assay reader.
Figure 4:
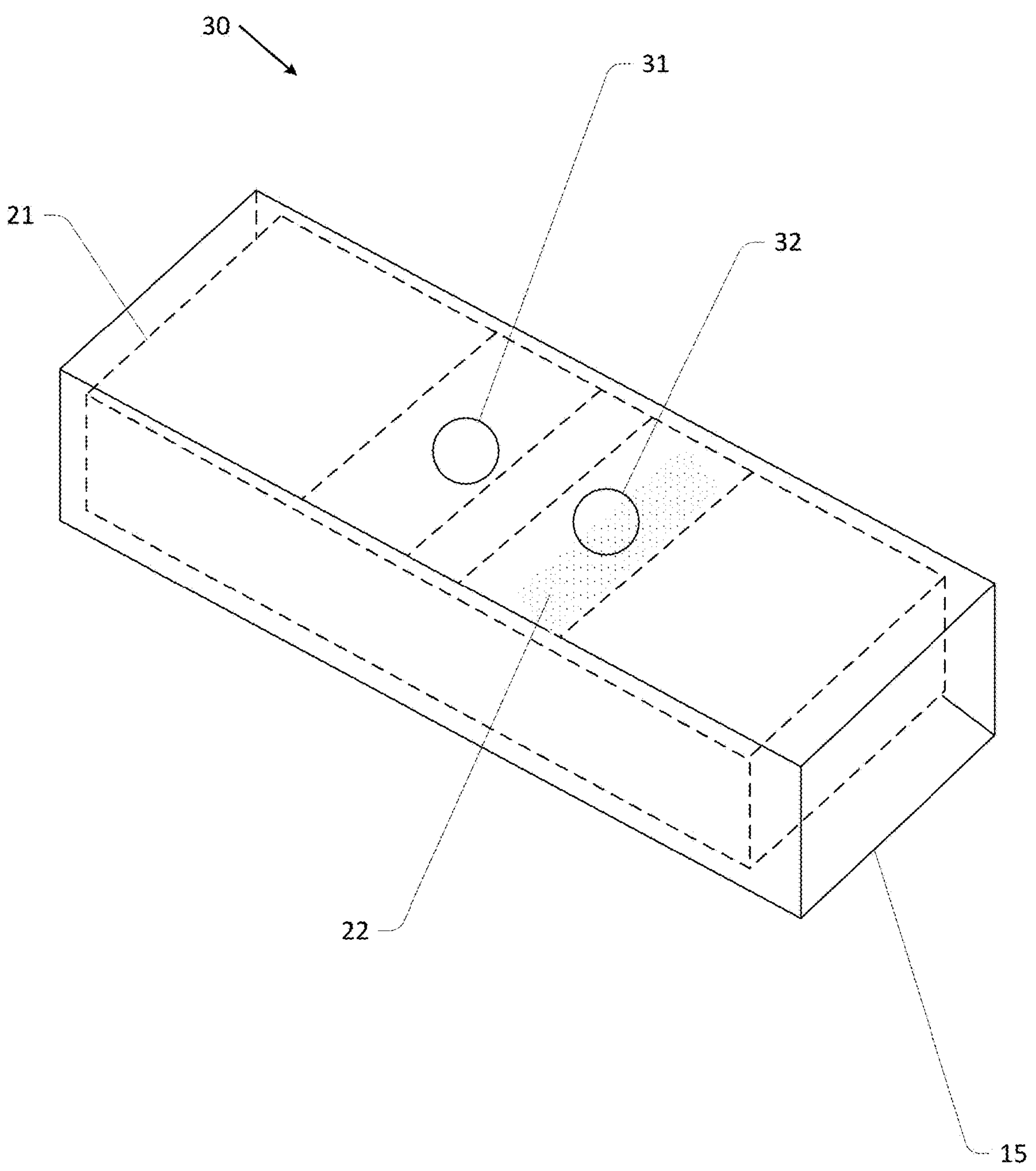
FIG. 4 is a perspective view of the biological-assay reader.

FIG. 3 shows a side view of the biological-assay reader and FIG. 4 shows a perspective view of the biological-assay reader (30). The biological-assay reader is inside the casing of the wearable device and is configured to read the biological sample from the biological-assay cartridge. The biological-assay cartridge (21) will be housed within the biological-assay reader (30) during the quantification of the biological sample on the test line (22). After applying the biological sample (e.g., saliva), the user will insert the biological-assay cartridge into the proposed wearable device via the biological-assay-reader entry port (15). During the process of sample quantification, a light source (31) will shine a predetermined concentration of light onto the test line (22). As the specific antigen absorbs the corresponding wavelength of the light source (31), the reflected wavelength of light will be measured using a light detector (32) such as light-dependent resistor or other light sensitive detectors, and the analog and digital data from the light detector (32) will be transmitted to computer processors for analysis.

Although FIGS. 3 and 4 depict a singular light source and light detector for the analysis of the biological-assay cartridge, it would be possible to integrate multiple light sources and light detectors into the wearable device for the quantification of multiple test lines within a single cartridge. Also, various types of analytes may require a specific wavelength of light for analysis. Thus, the light source (31) will have the ability to modify and/or filter the light shown on a test line (22) in order to satisfy the necessary wavelength of light needed. The analog and digital data retrieved from the light detector (32) will be processed using the microprocessor and interpolated to a specific voltage. The voltage identified will be the stated reference of the concentration of the specific analyte of interest.

Figure 5A:
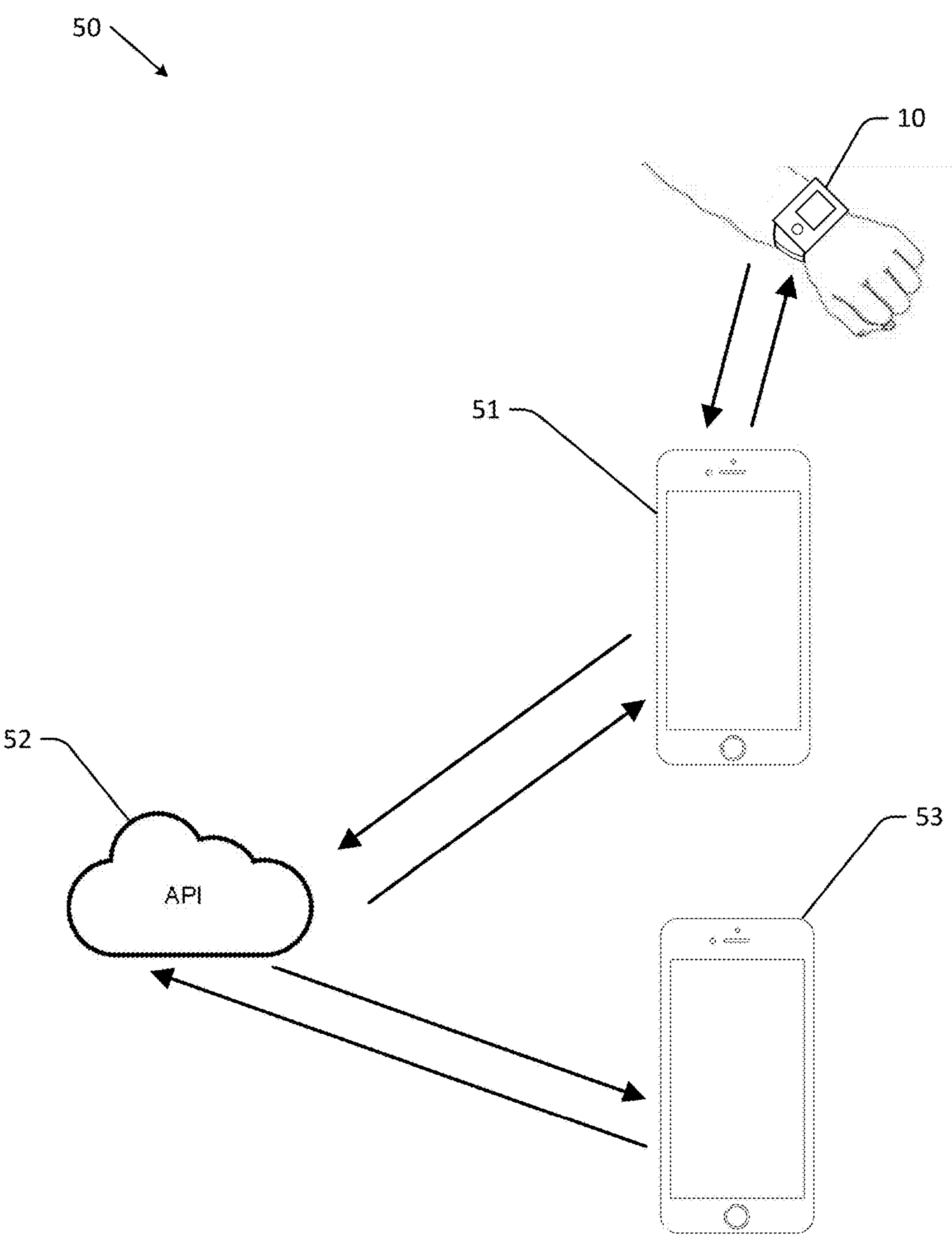
FIG. 5A is a diagram of the digital health system.

FIG. 5A is a diagram of the digital health system (50). The wearable device (10) will be worn on the body of the user. The user's MICD (e.g., smartphone) (51) will act as the computer processor and hub for the integrated biosensor system. The MICD has a processing unit and a system memory, which may include various forms of non-transitory storage media such as random access memory (RAM) and read-only memory (ROM). The MICD also may include nonvolatile storage memory, such as a hard disk drive, where additional data can be stored. The MICD will receive transmission of serial port data from the sensors via the radio or Bluetooth transceiver at specific preset intervals. When the data samples are received, the processor of the MICD will execute application programs that are designed to recognize specific sequences of data. All of the data received from the sensors will be uploaded to an encrypted API for easy portability. If programmatic Boolean checkpoints are confirmed or rejected (True or False statements), then feedback about sensor stability and performance will be transmitted from the MICD to the biosensor system where feedback about their performance can be displayed on the display.

The application interface on the MICD will also serve as an activity log for documenting the user's self-reported actions before and during the biological-sample readings. The MICD application will have the ability to calibrate the sensors and store the standardized values of the baseline in an Application Program Interface (API) (52). This will ensure accuracy and integrity of sensor readings while prolonging the effectiveness of the system's post-novel introduction. The GPS and built-in accelerometers of the phone will be utilized to document location and physical activity of participants during sensor recordings.

The API (52) will facilitate the performance of the biosensors by storing variables and recorded data, and it can be accessed by third parties via a third party's MICD (53) with a secure log-in and password. The programmatic language set in the API will allow users to register new accounts in the application and create a login username and password. This will provide security of the participants' personal data and restrict who has access to stored database. In addition to accessing databases of stored sensor data, the API also facilitates the calibration of sensors by executing periodic baselines of maximum and minimum values. For example, the API facilitates the calibration of biological-assay-reader sensor by taking measurement from a known concentration and producing an equation for standardizing the sensor readings. Because the API is executed from the server side of network, it would be easy to recalibrate sensors and update new algorithms if needed. The sharing of data will also be facilitated by the API. This will allow complete portability of users' data which will integrate and enhance the functionalities of the biosensor system.

The wireless communication between the wearable device and the MICD can be facilitated using a Bluetooth radio. For example, this technology is good for broadcasting data in close proximities and has short-wavelength UHF radio waves in the ISM band from 2.4 to 2.485 GHz. By using Bluetooth, the users will not be restricted to a laboratory setting or tethered to a computer in order to record sensor data. Instead, users will have complete mobility and may be monitored with a higher fidelity to typical daily activities in an uncontrolled/unrestricted environment.

Figure 5B:
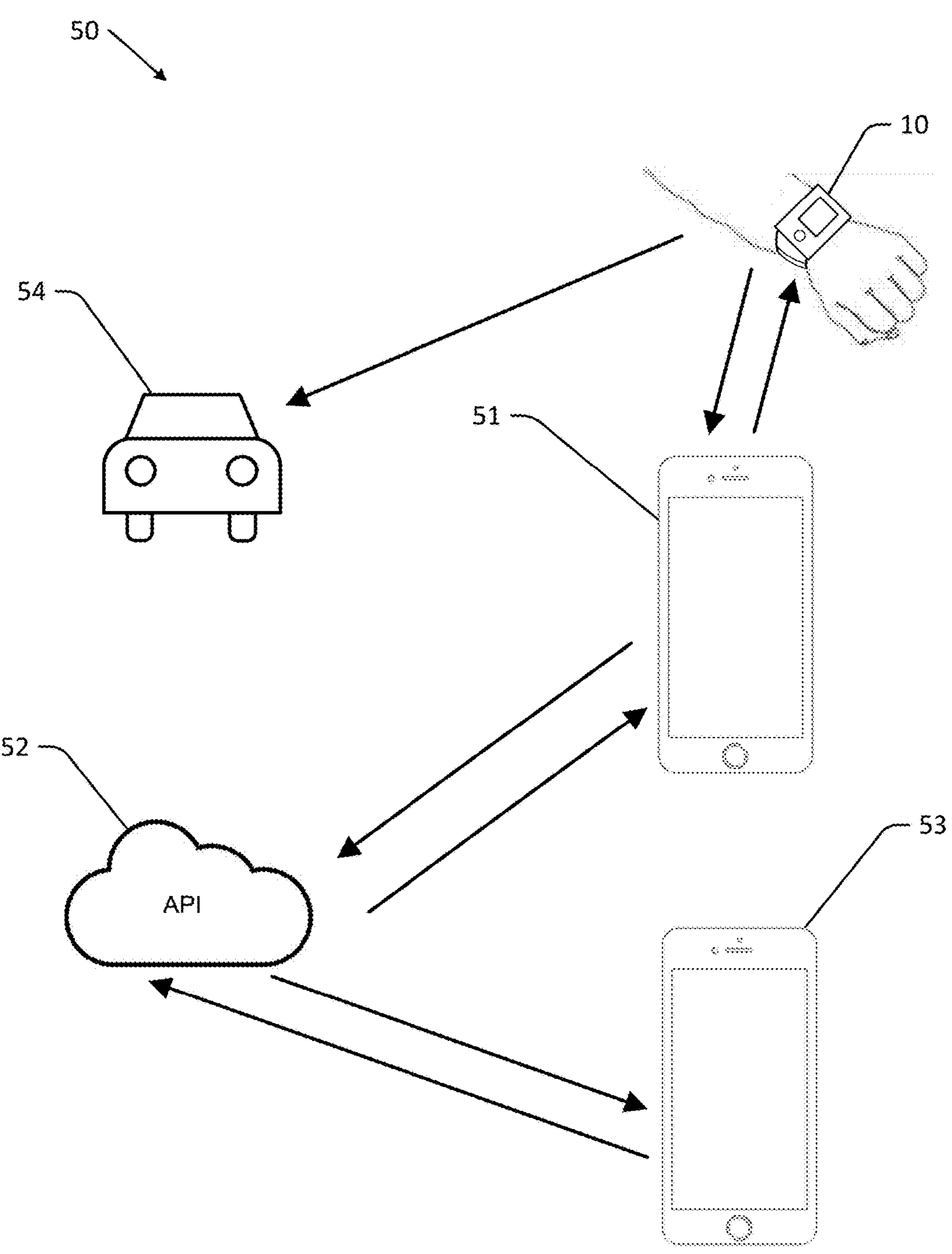
FIG. 5B is a diagram of the digital health system with MAID.

RFID (Radio-Frequency Identification) radio waves in the wearable device can be used to link the wearable device to the MICD, as well as to read and capture information from the biosensors and the MICD and link it with optional service components. For example, as shown in FIG. 5B, if a user exceeds the preset allowable blood alcohol concentration level, the MICD will store the event and submit a signal back to the wearable device where the Boolean checkpoint will fail (False) and the Monitoring Alcohol Interlocking Device (MAID) (54) RFID receiver will receive the execute command from the RFID transmitter in the wearable device to disable the user's vehicle. An added benefit of the RFID is that the signal can be received several feet from the wearable device. The MAID™ (Monitoring Alcohol Interlocking Device) (54) is an expandable optional service component that can be synchronized with the biosensor system. The unit is easily installed in a user's car to prevent intoxicated operation of the vehicle. Once data and user interactions are logged into the API (52), a third-party MICD (53) will be able to access information about the biosensors performance with a secure login and password. The third-party representative could be a medical doctor, parents, or even support counselors.

Figure 6A:
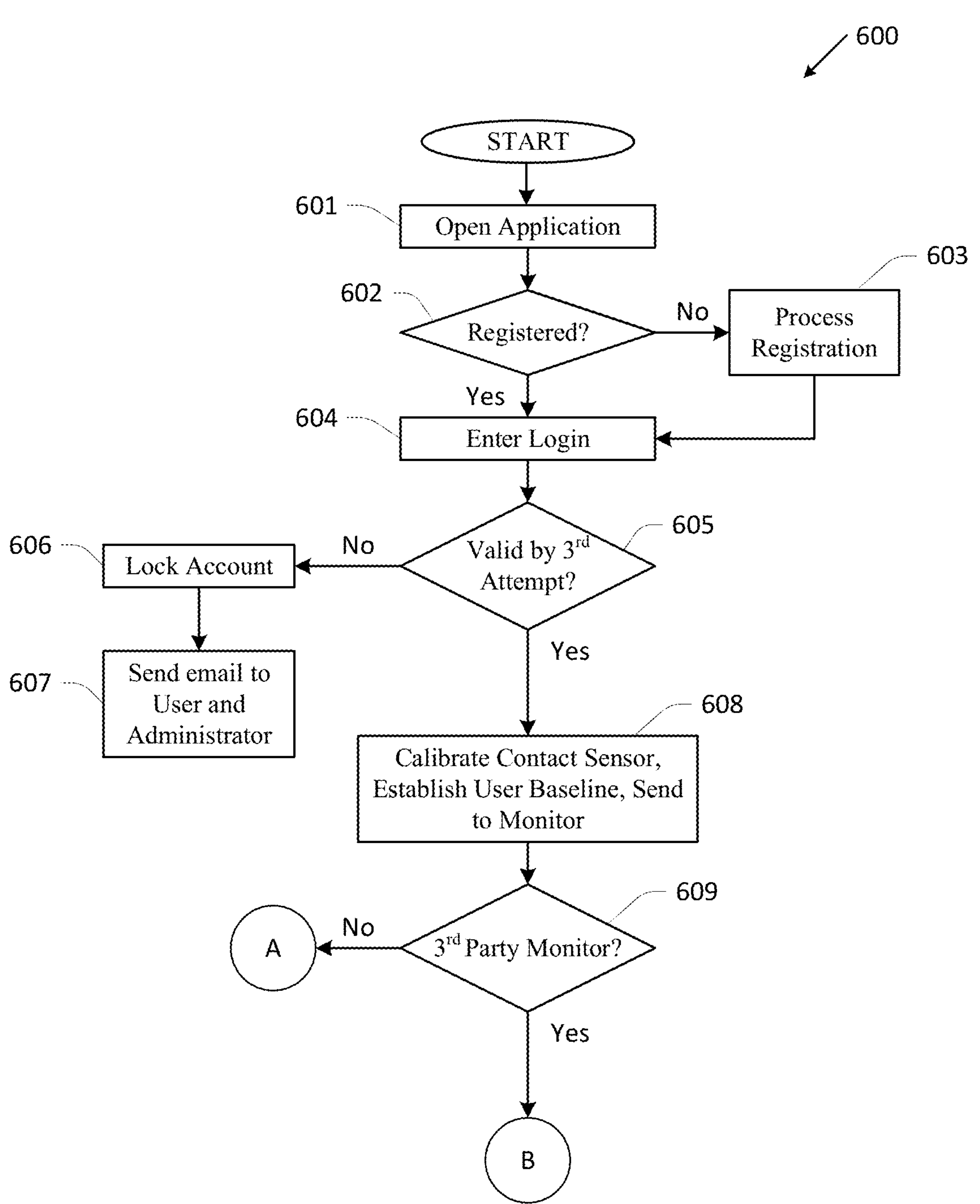
FIGS. 6A-6C is a flow diagram of the digital health system.
Figure 6B:
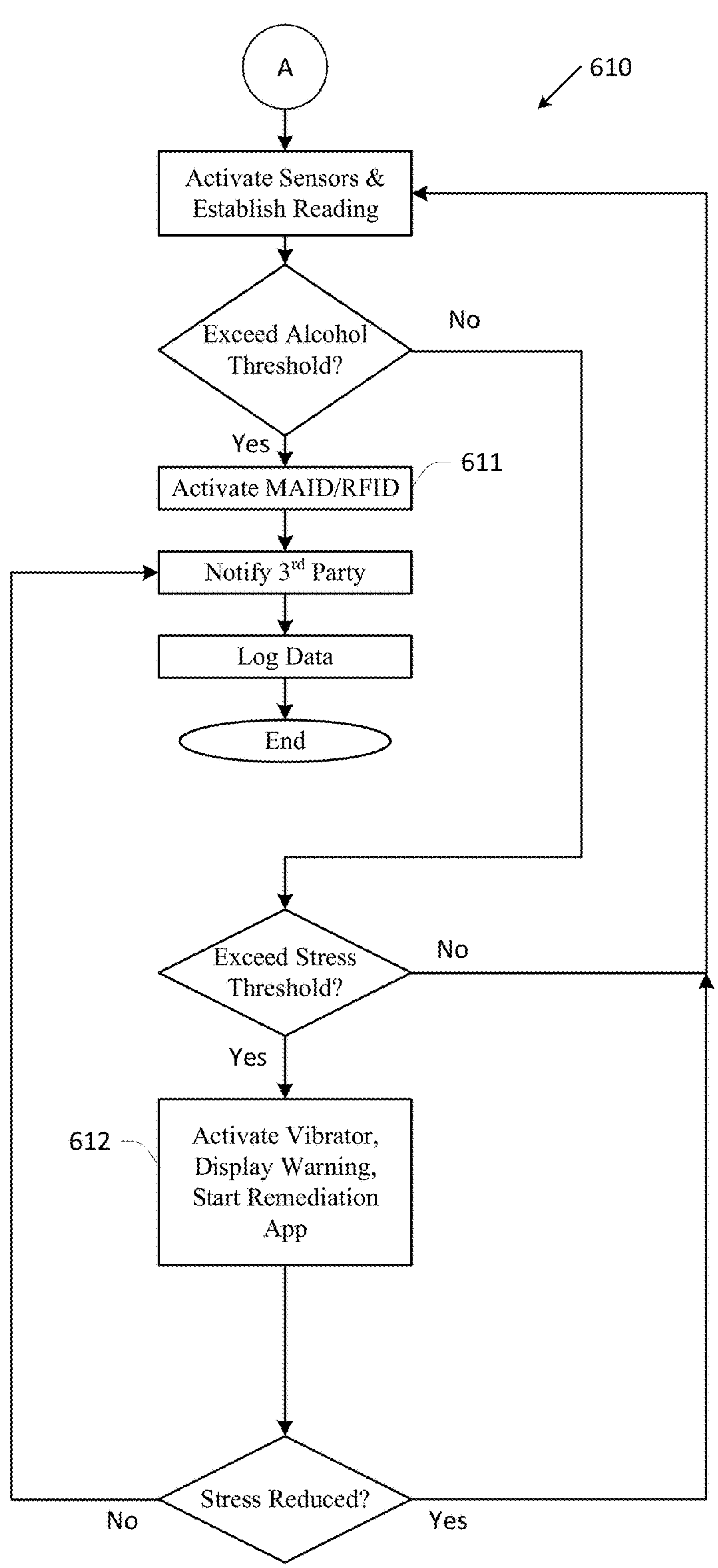
Figure 6C:
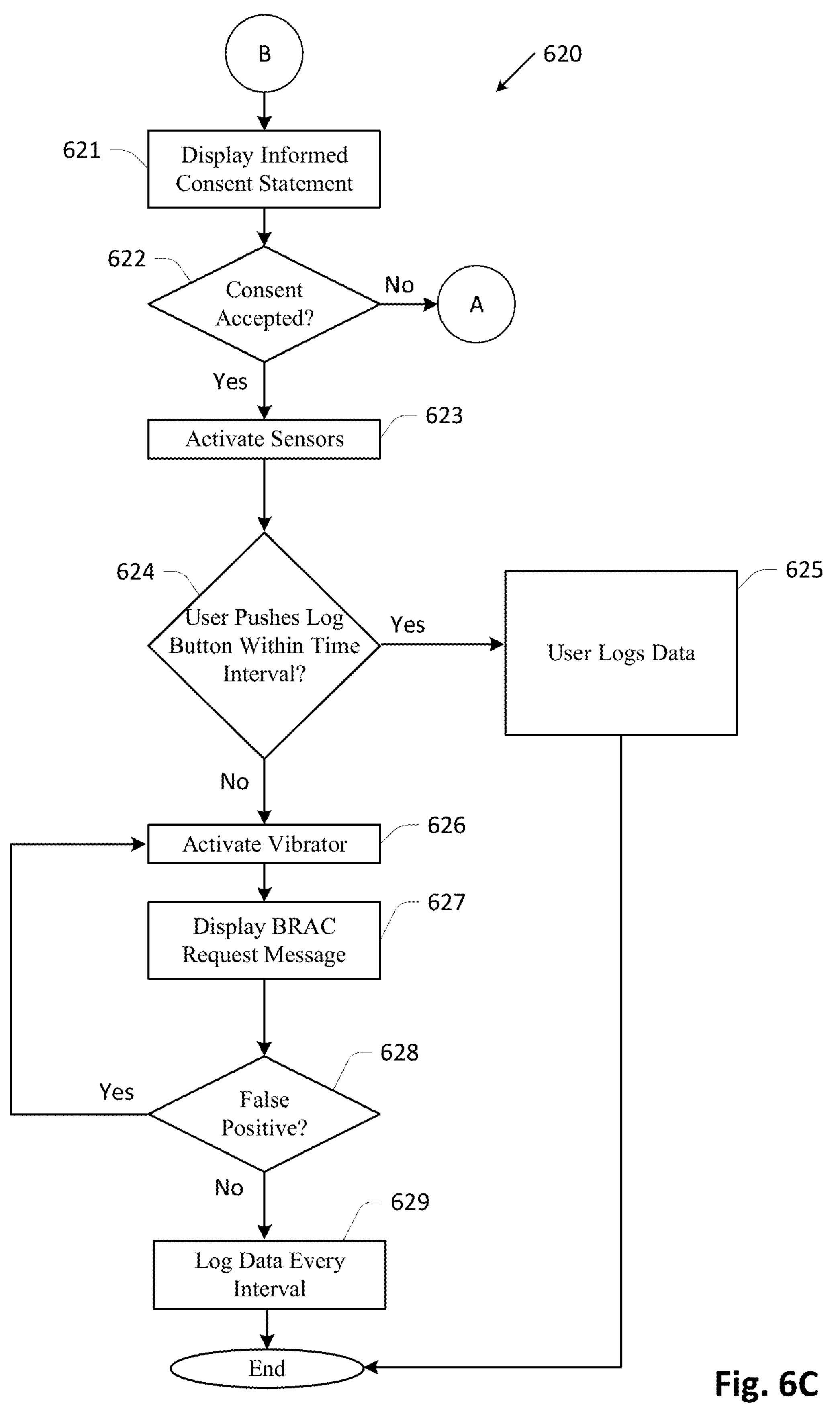

FIGS. 6A, 6B, and 6C show flow diagrams of the digital health system. The diagrams are one embodiment of the proposed digital health system. After attaching the wearable device to the body, the user will open the computer application for product services (601). If user is not registered (602), they will be prompted to create a unique username and password on their first instance of logging in (603). After registration, the user will be prompted to reenter their credentials for successful login (604). If the user entered an incorrect credential, they will be prompted to attempt again. Upon three consecutive unsuccessful attempts (605), the user's account will be locked (606) and an email with instructions will be sent to the user's registered email account (607). If the computer application recognized the username and password credential as valid, the hardware will undergo systematic calibration (608). First, the sensors will calibrate with a predetermined maximum and minimum value, followed by a measurement of the user's baseline. A successful notification will be sent to the API and third parties via the API. The system will conduct a cross-check to determine if the monitoring activity will be for research or self-monitoring mode (609).

FIG. 6B shows a flow diagram (610) of the digital health system in self-monitoring mode. If the service being offered is for self-monitoring, the sensors will activate and begin monitoring activity, as shown in FIG. 6B. The service provided in the self-monitoring mode is similar to the research mode—shown in FIG. 6C and described below—with the exception of in-application remediation (611), and the activation of the MAID and RFID (612).

FIG. 6C shows a flow diagram (620) of the digital health system in research mode. If the service being offered is for research, the user will be navigated to an informed-consent prompt screen (621). Once the user successfully accepts the consent statement (622), the monitoring service will begin (623). If the user declines the statement, they will be sent back to the opening portal of the program. In research mode, the wearable device will continuously monitor the activities of the biometric sensors on intervals of at least 15 minutes. After every cycle of 15 minutes, the vibrator will alarm (626), and the user will be requested for a sample. Parallel to vibrator alarming, the system will send a prompting message on the display screen (627). After submitting a sample, the application will determine if there was an instance of a false positive (628), and if so, will ask the user to resubmit a sample (627). If the sample was acceptable, the data will be logged to the API and saved in the database (629). In research mode the user will also have the ability to document self-reports about their condition and reaction to different stimuli. The user would push the log button on the application (624), and enter their corresponding feedback data (625). Once received, the feedback data will be logged in the API. The data logger will continue to document sensor activity in the API every cycle of 15 minutes.

Figure 7:
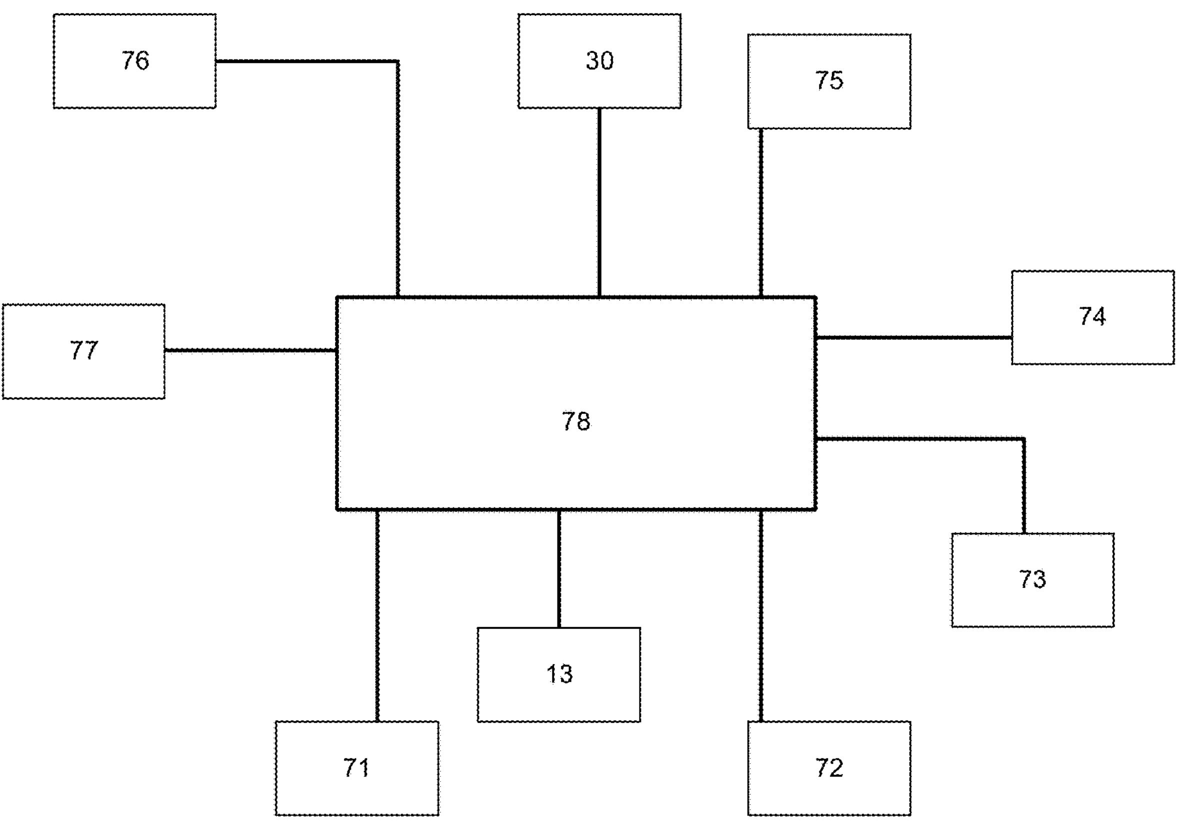
FIG. 7 is a block diagram of the proposed system wearable device configuration.

FIG. 7 is an illustrated block diagram of the proposed system wearable device configuration, with a display (13), portable power storage device (71), Bluetooth (72), skin & ambient temperature sensors (73), pulse sensor (74), galvanic skin resistance conductive sensors (75), biological-assay reader (30), a photovoltaic solar cell (76), a micro vibrator motor (77), and a microprocessor (78) such as a microcontroller or integrated computer programming device.

The wearable device will have a microprocessor (78) inside the casing of the wearable device to control program and algorithm execution, and will assist in detecting triggers that stimulate various physiological changes.

In order to provide continuous uninterrupted biosensor monitoring in an uncontrolled environment, it would be imperative to have a reliable powering system. The usage of a mini solar panel (76) will allow extended operation of the integrated system beyond normal battery capacity. Even though it is planned that the biosensor system will have low power consumption and will efficiently manage its available resources, the additional of a solar panel will provide higher confidence of continuous sample readings.

The utilization of the vibrator (77) will serve two purposes: (1) provide a private mode of alert and action prompting for users; and (2) act as a means of psychological behavior modification through self-monitoring. When preset perimeters are exceeded (stress), the vibrator will activate thus acting as a scolding mechanism.

Figure 8:
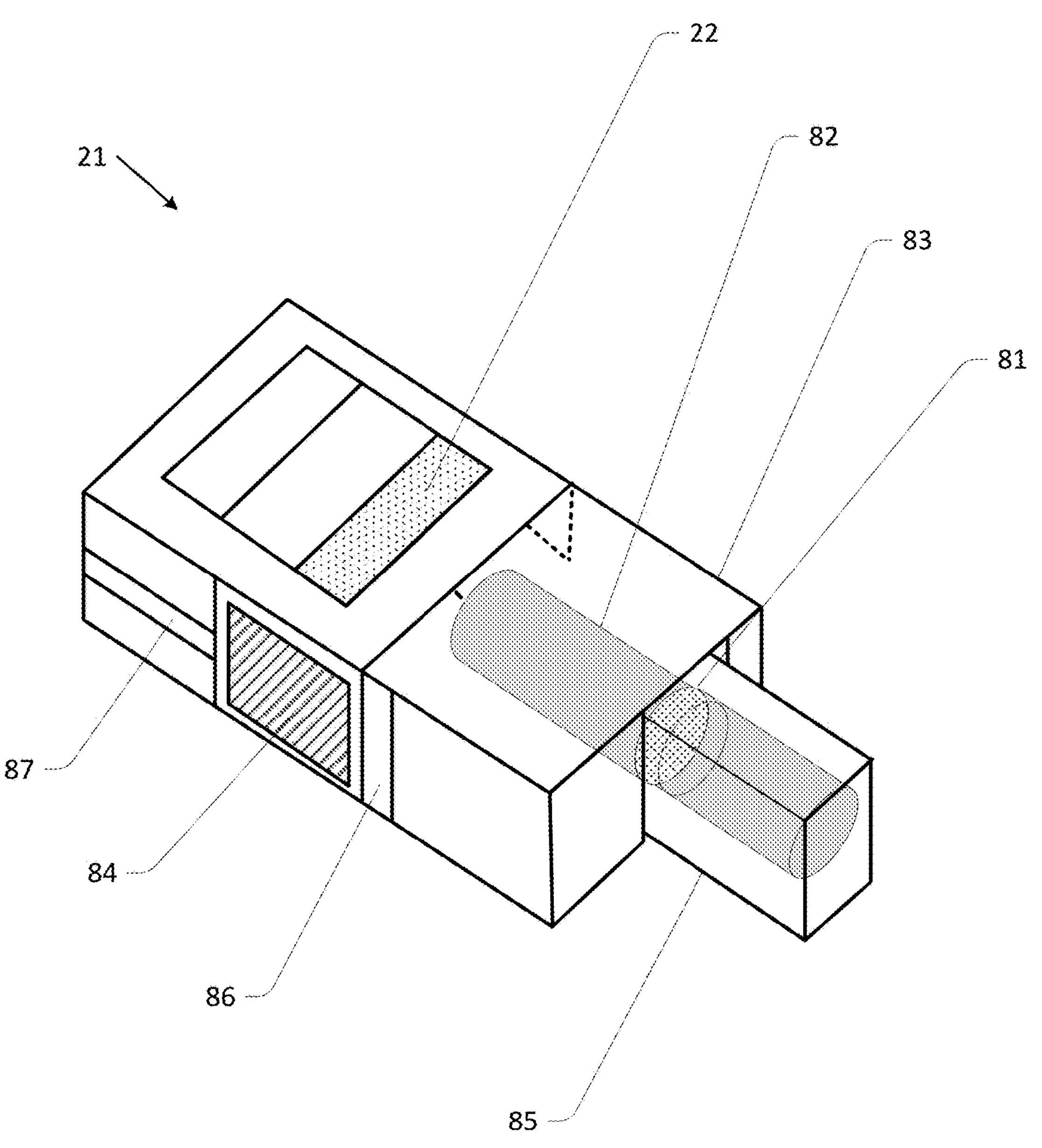
FIG. 8 is an illustration of the biological-assay cartridge with sample indicator and internal sample column.
Figure 9A:
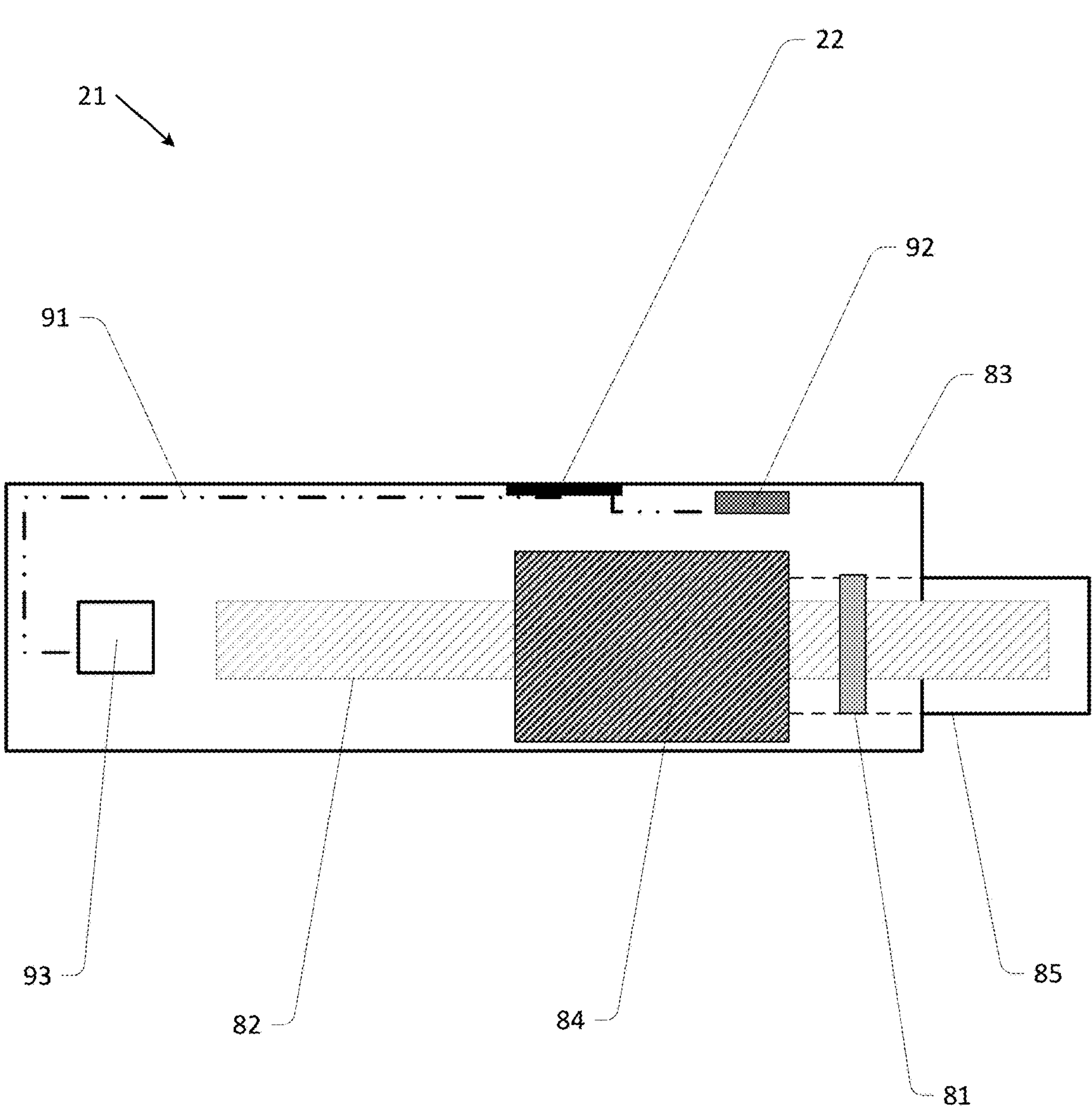
FIG. 9A is a side view of the biological-assay cartridge with extended absorbent sample pad.
Figure 9B:
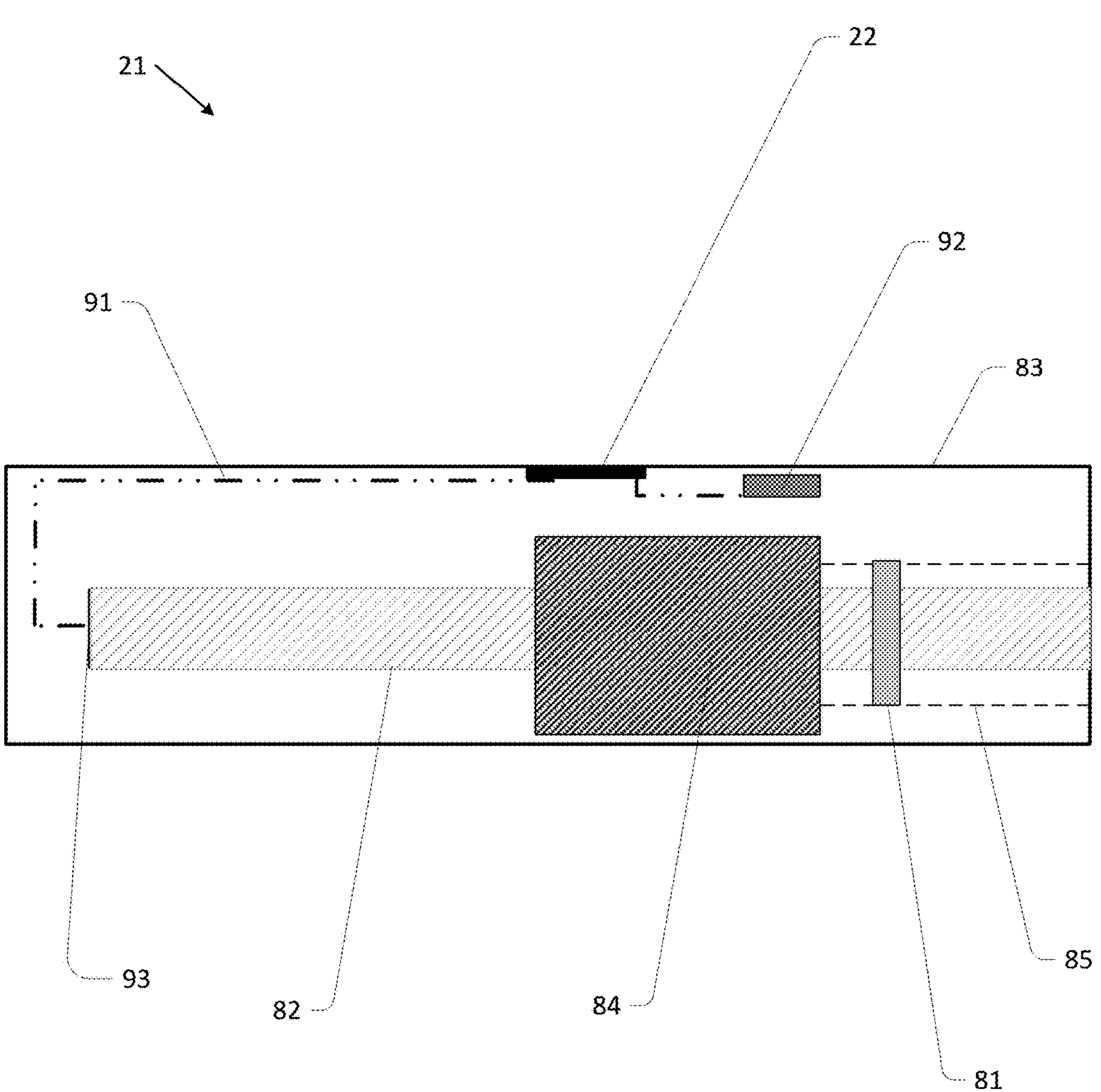
FIG. 9B is a side view of the biological-assay cartridge with the conjugated detection pad for specific analyte inside the internal sample column.

FIG. 8 shows the biological-assay cartridge with sample indicator and internal sample column, FIG. 9A shows a side view of the biological-assay cartridge with extended absorbent sample pad, and FIG. 9B shows a side view of the biological-assay cartridge with the conjugated detection pad for specific analyte inside the internal sample column. As depicted in the illustrated embodiments, there is shown a sample indicator (81), the internal sample column (82), the housing (83) for the sample pad and assay, retractable switch (84) for the sample pad, absorbent sample pad (85), the test line (22), a sample indicator viewport (86), and a switch track (87) for sliding the retractable switch back and forth. Additionally, FIGS. 9A and 9B show a membrane for passage of biological sample (91), and an absorbent sink pad (92) for excess sample or reagent. Illustrated in FIG. 9A is a conjugated detection pad (93) for at least one analyte of interest.

The absorbent sample pad (85) is designed to be retractable in the current embodiment, and allows for concealment of the sensitive internal sample column (82). There is a coating of a buffering solution for the absorbent sample pad (85) with chemical compounds (e.g., $NaHCO_3$, $C_5H_{12}O_5$). The buffering activity of the chemical compounds will assist in stabilizing the pH of the biological sample (e.g. saliva) to be between a pH of 5.5-8.1. This is essential in order to measure a high confidence to the presence of the specific analyte of interest. The sample indicator (81) will have a reactive compound that will react once wetted with biological sample. This reaction will display a specific color that will indicate that the biological sample is at an adequate volume for quantification. The sample indicator will continuously be housed in the housing (83), and will only be visible by looking through the sample indicator viewport (86). The internal sample column (82) will be fused to the absorbent sample pad (85), and may be repositioned using the retractable switch (84). The retractable switch may transverse across the switch track (87).

When a user is preparing to commence a test, they will apply biological sample to the absorbent sample pad (85) and retract the sample pad into the housing of the biological assay cartridge with the retractable switch (84). When the absorbent sample pad receives a biological sample, the sample will travel up the absorbent sample pad (85) and diffuse into the internal sample column (82). Once in the sample column (82), the biological sample will continue up the channel past the sample indicator line (81). When wetted, the indicator line (81) will display indication in the form of coloration that the volume of biological sample is adequate. The biological sample shall continue to transverse up the internal sample column (82). When a user retracts the sample pad (85), the motion will lock the conjugated detection pad for specific analyte (93) into the internal sample column (82) as illustrated in FIG. 9B. The biological sample will continue to move across the conjugated detection pad (93) and across the membrane (91) for passage of biological sample. Once wetted, the test line (22) will give a specific coloration depending upon the concentration of the analyte. The surplus of biological sample and reagent will be captured by the absorbent sink pad (92).

The known predicate laboratory equipment used for the quantification of biological samples includes high performance liquid chromatography (HPLC) and gas chromatography mass spectroscopy (GCMS). These types of equipment require skilled technicians and scientists to operate them efficiently. In addition, the capital investment for such equipment may be thousands of dollars. High-end laboratory equipment also have a lack of portability. Another method used for quantifying biological samples is the lateral-flow immunochromatic assay (LFA). Typically, a user would apply their biological sample to the sample pad of the cartridge which utilizes capillary flow to traverse the sample throughout the assay. Upon interaction with the gold nanoparticle conjugated antibodies, the sample containing antigen would bond to the test line site. Any remaining sample material would flow to the antibody to antibody site on the control line. The LFA technique is easy to operate and is very cost-effective. The noted disadvantages of this technique includes lag time of several minutes between sampling and obtaining the results, and the inability to quantitate the sample directly.

The aforementioned embodiment of the proposed device is intended to be non-invasive and specific for biological testing.

Figure 10:
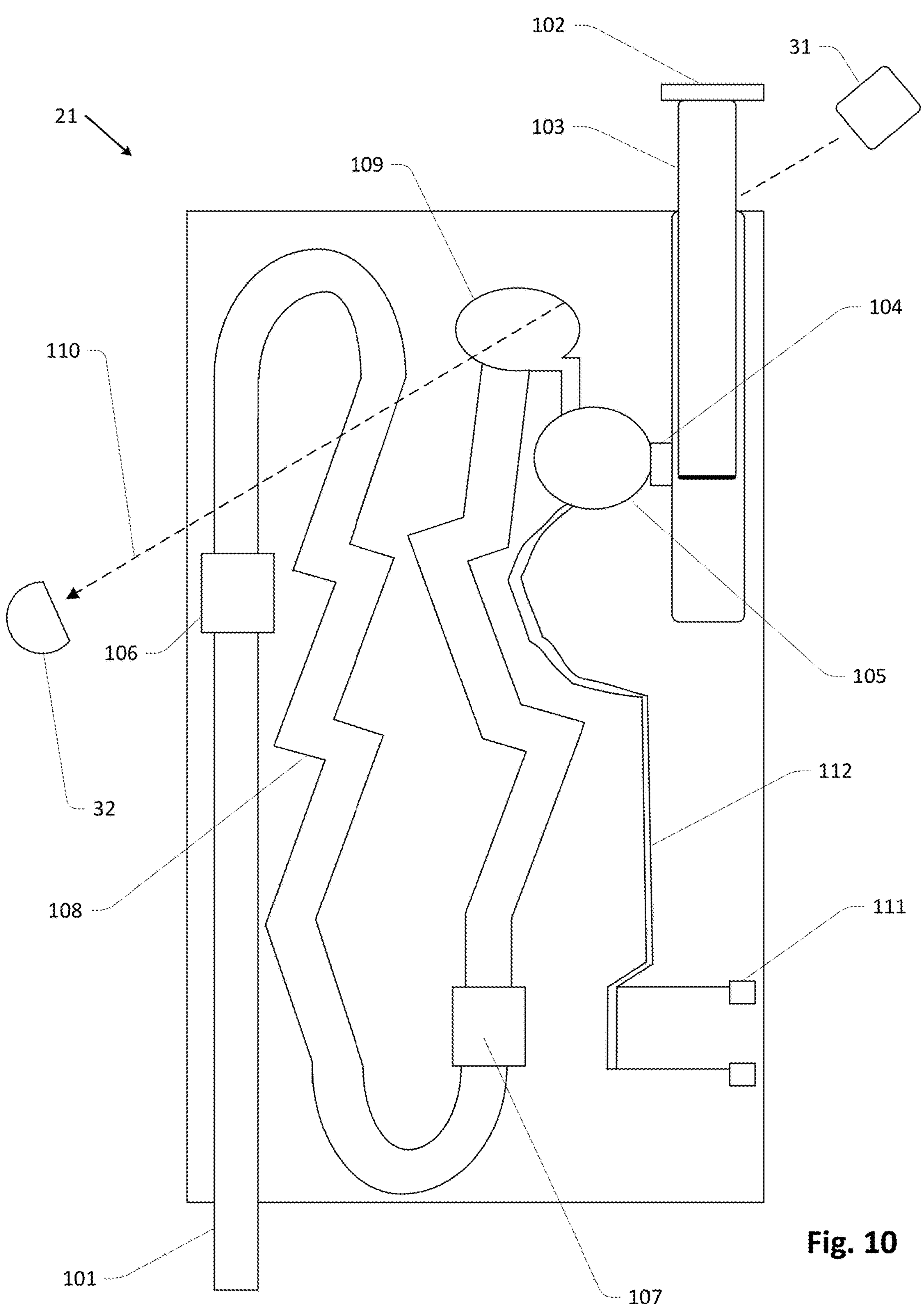
FIG. 10 is an illustration of the biological-assay cartridge with analysis chamber, and the biological-assay-reader light source and light detector.

FIG. 10 shows an illustration of the biological-assay cartridge (21). In order to retrieve a biological sample, a user will insert the sampling port (101) into their mouth while placing their finger upon the plunger base (102) and pressing with a continuous motion until the plunger shaft (103) is completely depressed. When the plunger shaft is completely depressed, it will create a vacuum at the vacuum port (104), thereby causing the flow of biological sample (saliva) to purge into the channel of the cartridge. The diameter and specific flowrate of the cartridge should be sufficient to obtain approximately 50 μl of sample material. The flowrate check valve (105) controls the flowrate of the biological sample into the channel. It should be calibrated to match the specific pressure needed to obtain 50 μl of sample material. The biological sample will first be treated with a buffer agent to stabilize pH. The buffer agent site (106) has immobilized chemicals that has been coated to the interior of the sample channel. The antibody conjugate particles site (107) has immobilized nanoparticles (i.e. gold nanoparticles) that has been coated to the interior of the sample channel. The vacuum pressure will cause the biological sample to flow throughout the channel. The biological sample will mix with the buffer and antibody conjugate particle by continuous agitation with the serpentine mixer (108), and will continue to flow into the analysis chamber (109).

FIG. 10 also shows a light source (31), a light detector (32), and the pathway of light transmission (110) through the cartridge via passage of the analysis chamber (109).

The analysis chamber allows optical quantification of the complete sample (biological sample+buffer+conjugate particles) by allowing a specific wavelength of light from a light source (31) to penetrate the sample. The analysis chamber is transparent, thereby allowing light from a light source (31) to be transmitted. The exiting light (110) will be quantified with a light detector (32) and converted to electrical voltage for biological sample quantification. As a means of providing high specification and rapid analysis of biological sample quantification, the present invention will systematically quantify biological samples utilizing electrochemistry. Following the quantification of the biological sample with the optical sensor assembly, the electrical reference probe (111) will pulse the complete biological sample with a specific voltage of electricity, and the reference probe will measure the resistance of the complete biological sample through the test column (112). The sample resistance will be calibrated with a reference voltage to quantitate the concentration of the biological sample.

Figure 11:
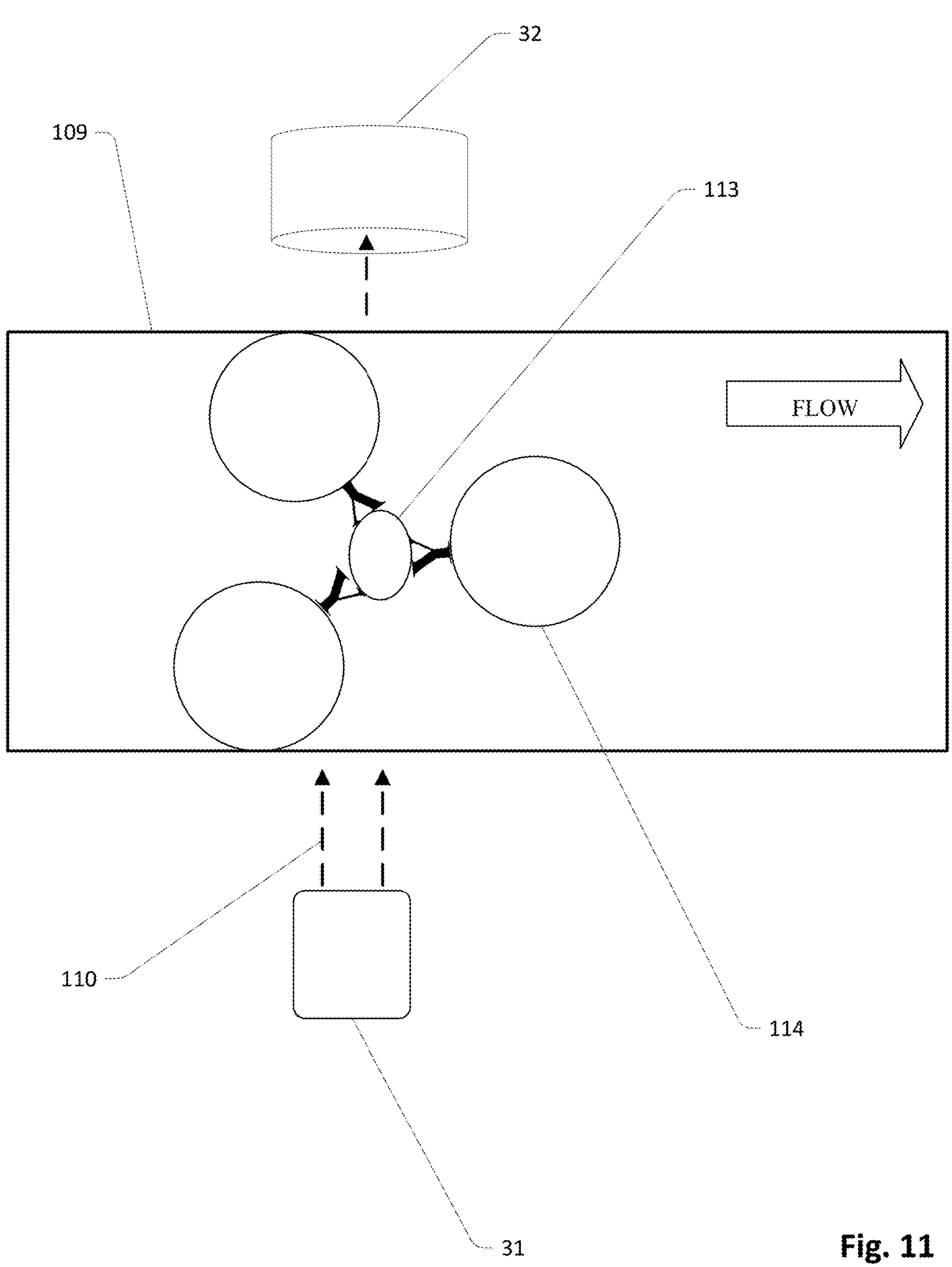
FIG. 11 is an illustration of the analysis chamber in the biological-assay cartridge.

FIG. 11 shows a light source (31), the light detector (32), the analysis chamber (109), the biological-sample antigen (113), the antibody conjugate particle (114), and the light transmission (110). The biological sample antigen (113) will bond with the antibody conjugate particles (114) thus forming a complex particle structure with increased conjugate to antigen footprint. The complex particle structure will be able to bend light at an angle dependent upon the concentration of the biological sample, thus allowing the light detector (32) to measure the transmitted light while minimizing the interference of signal to noise ratio of the light source. This method increases the specificity and sensitivity of biological sample analysis.

The present invention overcomes the aforementioned disadvantages of high-end laboratory equipment by providing an integrated system capable of quantifying specific analyte (e.g., cortisol) in real-time. The present invention offers advantageous over predicate laboratory equipment such as lower capital investment, simple operation by untrained person, high precision, and selectivity for sampling. In addition, the present invention utilizes a closed-system embedded quantification assay that allows rapid analysis of biological samples with high sensitivity.

Each step of the diagrams, flowcharts, and control-flow illustrations can be implemented by computer-program instructions or other means. Although computer-program instructions are discussed, an apparatus or system according to the present invention can include other means, such as hardware or some combination of hardware and software, including one or more processors or controllers, for performing the disclosed functions.

In this regard, the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer such as smartphones, tablets, and smart watches can include a processing unit and a system memory, which may include various forms of non-transitory storage media such as random access memory (RAM) and read-only memory (ROM). The computer also may include nonvolatile storage memory, such as a hard disk drive, where additional data can be stored.

The above-mentioned components of the mobile application unit are to be interpreted in the most general manner. For example, the processor can include a single physical microprocessor or microcontroller, a cluster of processors, a datacenter or a cluster of datacenters, a computing cloud service, and the like.

In a further example, the non-transitory memory can include various forms of non-transitory storage media, including random access memory and other forms of dynamic storage, and hard disks, hard disk clusters, cloud storage services, and other forms of long-term storage. Similarly, the input/output can include a plurality of well-known input/output devices, such as screens, keyboards, pointing devices, motion trackers, communication ports, and so forth. This can include system access to common functions and hardware, such as for example via operating system layers such as Windows, Linux, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

In a related embodiment, the wearable device can communicate over a network, a set of network connections, or direct connections, which can include the general Internet, a Wide Area Network or a Local Area Network, or another form of communication network, transmitted on wired or wireless connections. Wireless networks can for example include Ethernet, Wi-Fi, Bluetooth, ZigBee, and NFC.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams, or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, steps of the block diagram, flowchart or control flow illustrations support combinations of means for performing the specified functions, combinations of steps for performing the specified functions and program instruction means for performing the specified functions. It will also be understood that each block or step of the diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

The invention claimed is:

1. A device, comprising:

a casing comprising an entry port;

a biological-assay cartridge comprising a housing:

the entry port being adapted to receive the biological-assay cartridge;

the biological-assay cartridge being configured to receive a biological sample comprising analytes wherein the biological-assay cartridge comprises a sampling port for obtaining the biological sample, the sampling port being located outside the housing, a plunger shaft for creating a vacuum to obtain the biological sample through the sampling port, a vacuum port configured to cause the flow of the biological sample into a channel within the cartridge, and a flowrate check valve configured to control the flowrate of the biological sample into the channel;

contact sensors formed on an outer portion of the casing; and a biological-assay reader placed inside the casing configured to read the biological sample, wherein the biological-assay reader comprises:

at least one light source for directing light onto the biological sample; and at least one light detector for identifying a concentration of an analyte in the biological sample by analyzing light emitted from the biological sample in response to the light directed from the source.

2. The device of claim 1, wherein the biological-assay cartridge further comprises a test line for the biological sample, the test line being visible from the outside of the housing, and the test line being configured to display information about one or more analytes in the biological sample.

3. The device of claim 2, wherein the biological-assay cartridge further comprises:

a first membrane for passage of the biological sample to the test area; and a second membrane for passage of the biological sample from the test area.

4. The device of claim 1, wherein the light source transmits light of a predetermined wavelength.

5. The device of claim 1, wherein the light detector measures the light reflected by the biological sample.

6. The device of claim 5, wherein the biological sample reflects light at an angle dependent upon the concentration of the analyte in the biological sample, and the light detector is used to analyze the angle of the reflected light.

7. The device of claim 6, wherein the light detector measures the intensity of the light emitted by the biological sample.

8. The device of claim 1, wherein the biological-assay cartridge further comprises:

a site inside the housing for binding the analytes within the biological sample.

9. The device of claim 8, wherein the biological-assay cartridge further comprises a transparent analysis chamber configured to receive the biological sample, the transparent analysis chamber being configured to allow light from the light source to be transmitted through the transparent analysis chamber and onto the biological sample, and to allow the light emitted from the biological sample to be analyzed by the light detector.

10. The device of claim 9, wherein the biological-assay cartridge further comprises a mixer for mixing the biological sample.

11. The device of claim 8, wherein the biological-assay cartridge further comprises an electrical reference probe configured to measure resistance of the mixture of the biological sample, and an electrochemical test configured to measure analytes in the biological sample.

12. The device of claim 1, wherein the biological sample is a bodily fluid.

* * * * *